Figure 1:
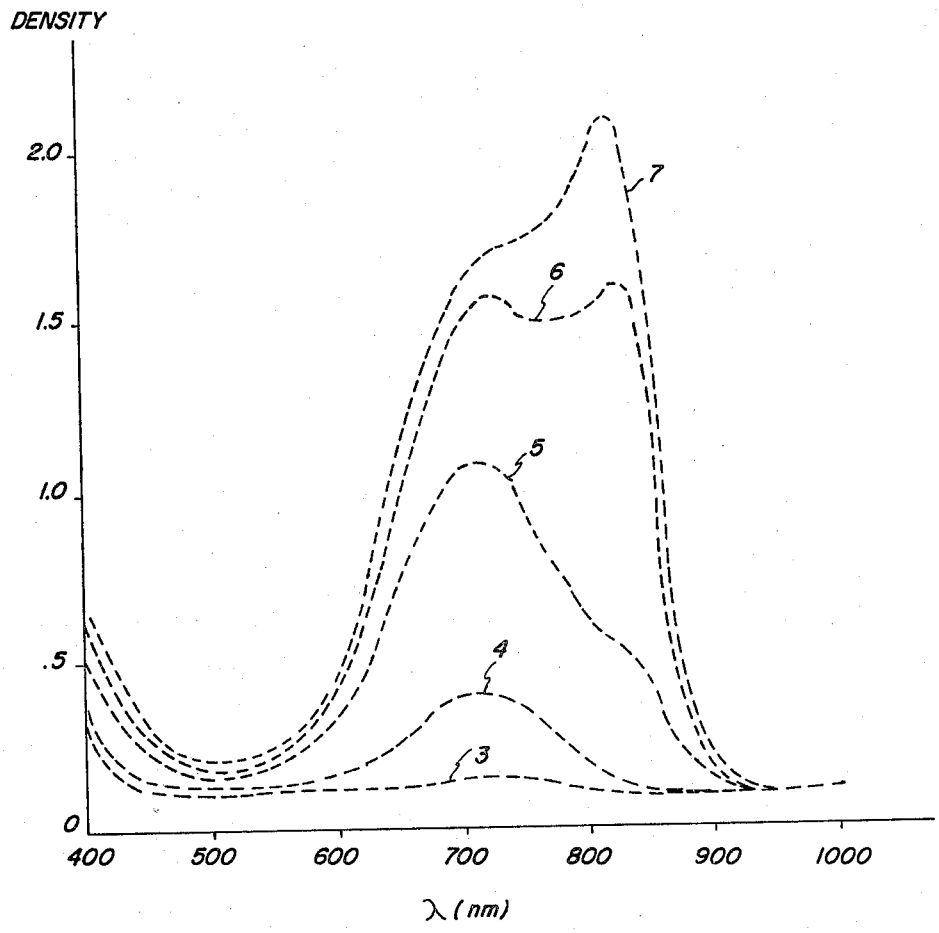
Figure 2:
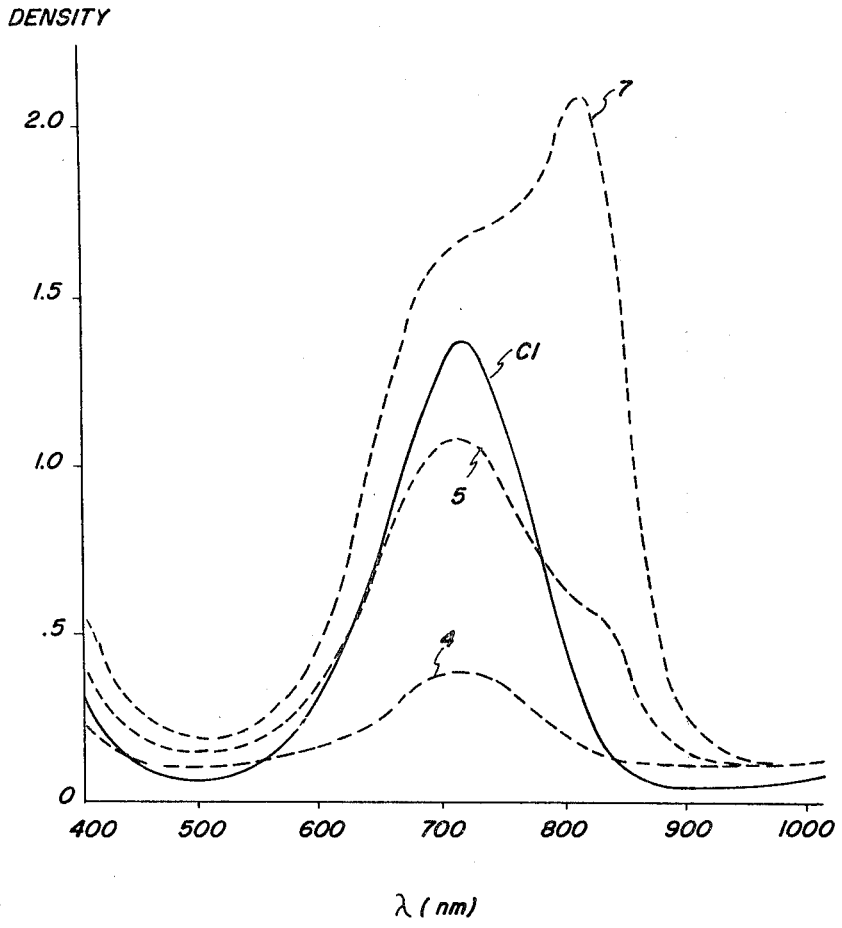
Figure 3:
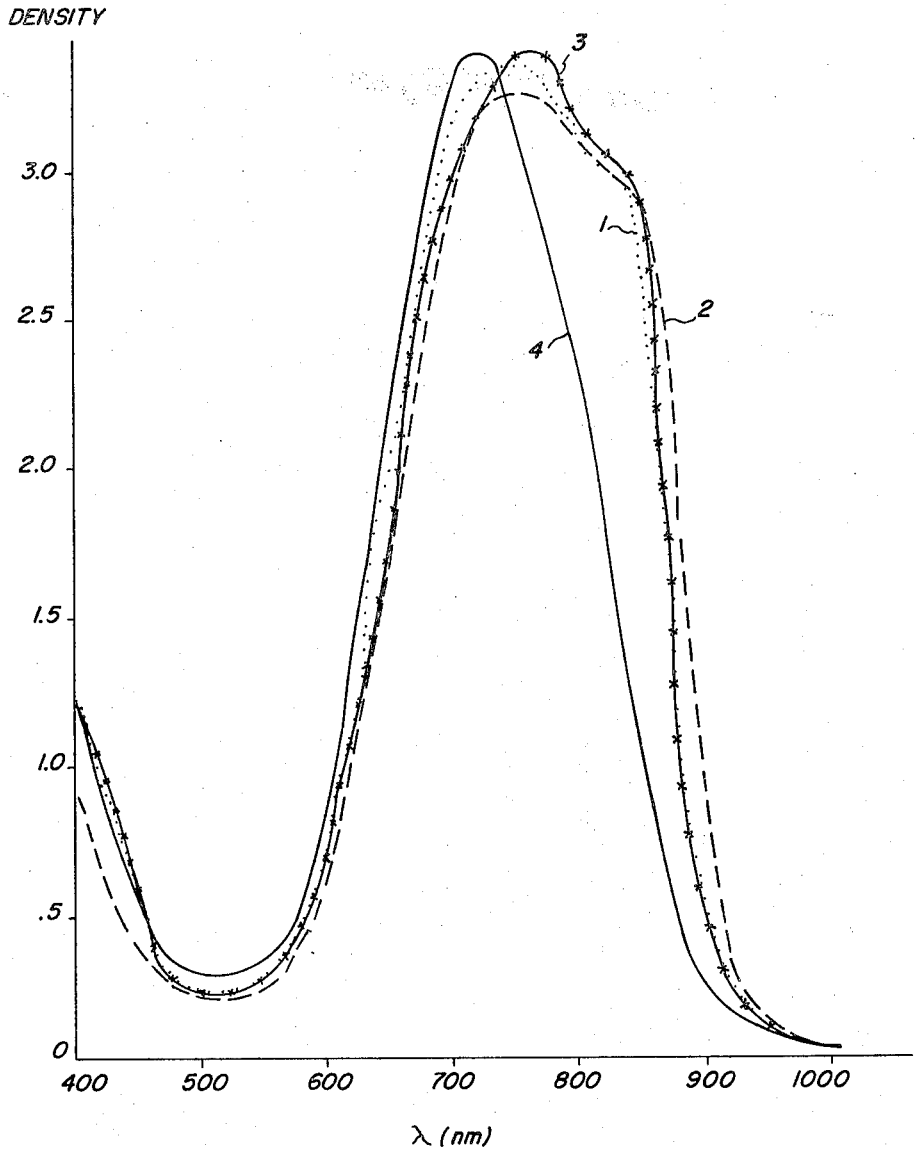
Figure 4:
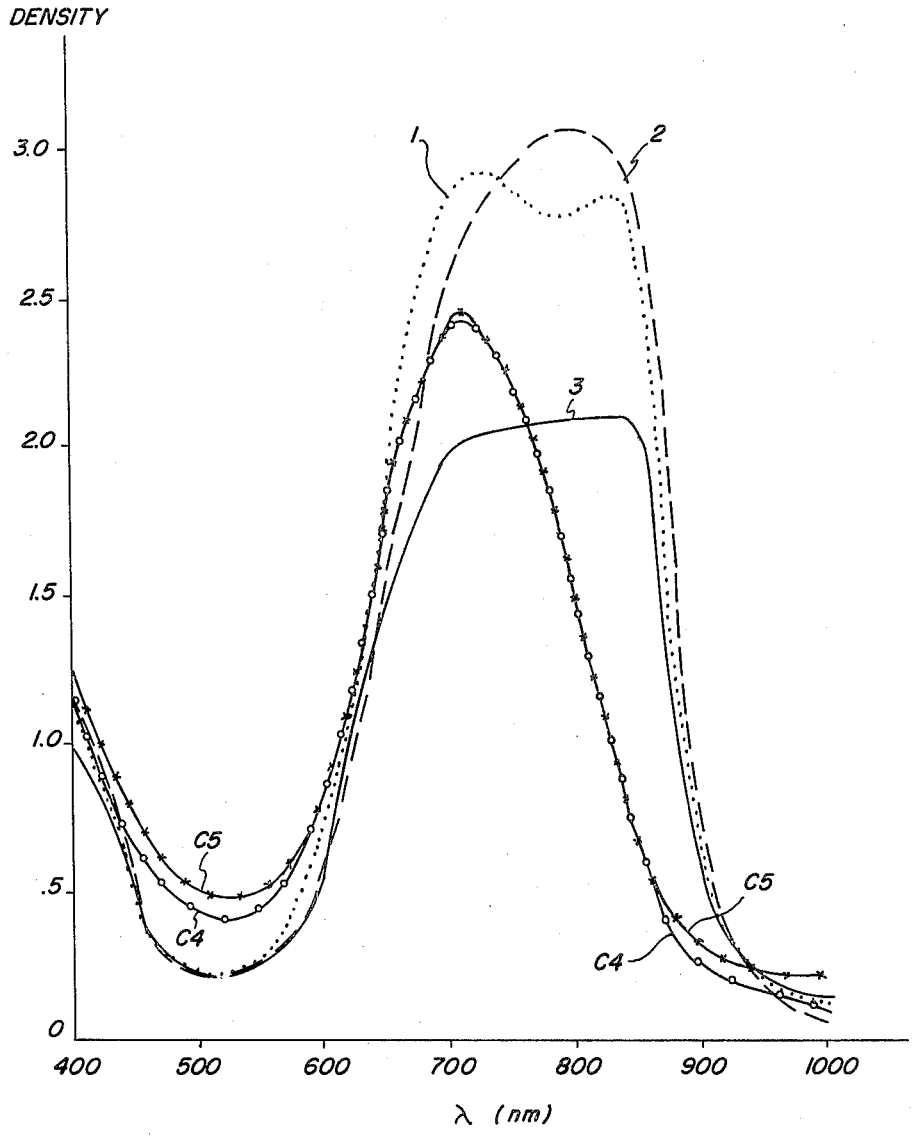

United States Defensive Publication [19] (H) [11] T998,014

Ciurca, Jr. et al. [43] Sep. 2, 1980

[54] THIOAZOLYL COUPLERS, COUPLER COMPOSITIONS AND PHOTOGRAPHIC ELEMENTS SUITED TO FORMING INTEGRAL SOUND TRACKS

[75] Inventors: Samuel J. Ciurca, Jr., Rochester; Robert G. Cameron, Spencerport; Edward J. Walsh, Pittsford, all of N.Y.

[73] Assignee: Eastman Kodak Company, Rochester, N.Y.

[21] Appl. No.: 21,754

[22] Filed: Mar. 19, 1979

Related U.S. Application Data

[62] Division of Ser. No. 928,621, Jul. 27, 1978, Pat. No. 4,178,183.

[51] Int. Cl.[3] ..... C07D 277/38

[52] U.S. Cl. ..... 548/195

[57] ABSTRACT

Ballasted 1-hydroxy-2-naphthamide couplers which are N-substituted with a thiazolyl group that is in turn substituted with a phenyl group are disclosed as well as compositions and photographic elements containing these couplers in coupler solvents. Preferred couplers are those of the formula

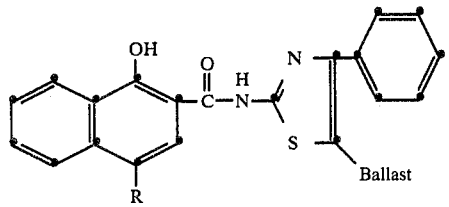

wherein R is a coupling-off group and Ballast is a hydrophobic photographic ballasting group. The coupler solvent particles are comprised of a combination of a coupler solvent and the coupler capable of permitting the formation of a microcrystalline dye. Surprisingly these microcrystalline dyes exhibit a broadened absorption characteristic in the 750 to 850 nm region of the spectrum. Dye images having such absorption characteristics are particularly suited to forming integral infrared absorbing sound tracks in photographic elements, such as motion picture projection films.

3 Claims, 4 Sheets Drawing,

38 Pages Specification

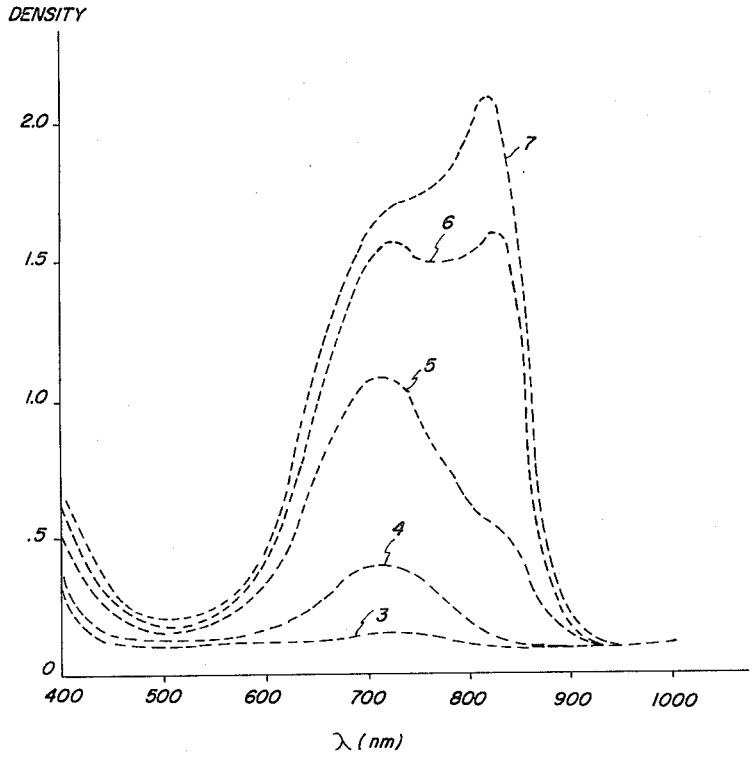

The file of this unexamined application may be inspected and copies thereof may be purchased (849 O.G. 1221, Apr. 9, 1968).